US012721586B2

(12) United States Patent
Ono

(10) Patent No.: US 12,721,586 B2
(45) Date of Patent: Sep. 1, 2026

(54) INFORMATION OUTPUT APPARATUS, INFORMATION PROCESSING APPARATUS, RECORDING MEDIUM, INFORMATION OUTPUT METHOD, AND INFORMATION PROCESSING METHOD

(71) Applicant: Konica Minolta, Inc., Tokyo (JP)

(72) Inventor: Kojiro Ono, Narita (JP)

(73) Assignee: KONICA MINOLTA, INC., Tokyo (JP)

( * ) Notice: Subject to any disclaimer, the term of this patent is extended or adjusted under 35 U.S.C. 154(b) by 81 days.

(21) Appl. No.: 18/425,523

(22) Filed: Jan. 29, 2024

(65) Prior Publication Data

US 2024/0260925 A1 Aug. 8, 2024

(30) Foreign Application Priority Data

Feb. 6, 2023 (JP) ................................. 2023-015757

(51) Int. Cl.
*A61B 6/00* (2024.01)

(52) U.S. Cl.
CPC .................................... *A61B 6/542* (2013.01)

(58) Field of Classification Search
CPC ...................................................... A61B 6/542
See application file for complete search history.

(56) References Cited

U.S. PATENT DOCUMENTS

2013/0077744 A1* 3/2013 Kamiya ................. A61B 6/548 378/62
2014/0079310 A1* 3/2014 Nakatsugawa ........ A61B 6/542 382/132
2014/0093043 A1* 4/2014 Nakatsugawa .......... A61B 6/58 378/62

FOREIGN PATENT DOCUMENTS

JP 2011-156346 A 8/2011
JP 6860113 B1 4/2021
JP 2022-77799 A 5/2022

OTHER PUBLICATIONS

Office Action, dated May 19, 2026, which was issued for the corresponding Japanese Patent Application No. 2023-015757, 6 pages, with English translation.

* cited by examiner

*Primary Examiner* — Dani Fox
(74) *Attorney, Agent, or Firm* — LUCAS & MERCANTI, LLP

(57) ABSTRACT

An information output apparatus comprising: a hardware processor that outputs information based on a number of simple X-ray imaging operations as information pertaining to a continuous imaging dose, the continuous imaging dose being a dose in a series of X-ray imaging operations.

19 Claims, 6 Drawing Sheets

FIG.8

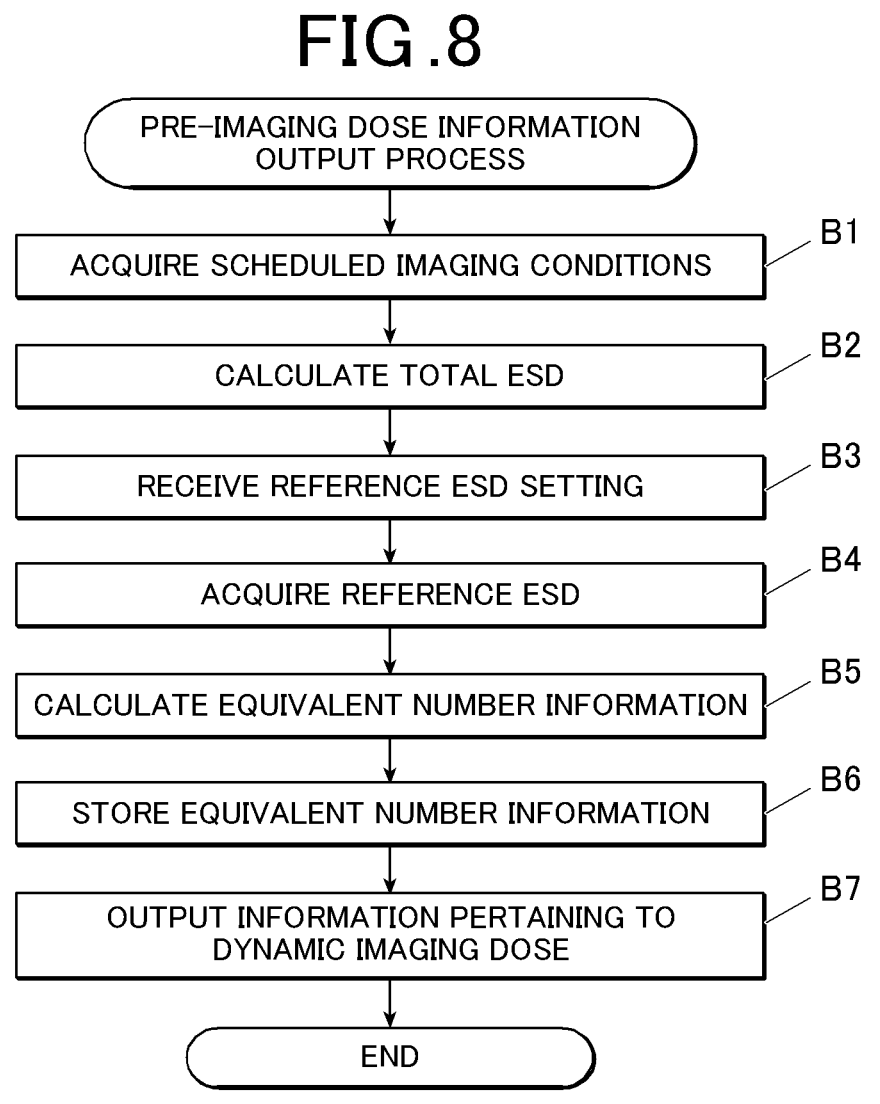

PRE-IMAGING DOSE INFORMATION OUTPUT PROCESS

B1 ACQUIRE SCHEDULED IMAGING CONDITIONS

B2 CALCULATE TOTAL ESD

B3 RECEIVE REFERENCE ESD SETTING

B4 ACQUIRE REFERENCE ESD

B5 CALCULATE EQUIVALENT NUMBER INFORMATION

B6 STORE EQUIVALENT NUMBER INFORMATION

B7 OUTPUT INFORMATION PERTAINING TO DYNAMIC IMAGING DOSE

END

EXAMINATION LIST

22b

| EXAMINATION DATE AND TIME ▼ | PATIENT ID | PATIENT NAME (KANJI) | PATIENT NAME (KANA) | DATE OF BIRTH | PATIENT AGE | GENDER | EXAMINATION AGE | NUMBER OF IMAGINGS | EXAMINATION DESCRIPTION | TOTAL ESD AGGREGATE VALUE [mGy] | EQUIVALENT NUMBER INFORMATION AGGREGATE VALUE |
|---|---|---|---|---|---|---|---|---|---|---|---|
| 2021/01/05 16:04:12 | 00008 | YAMAMOTO, GORO | YAMAMOTO, GORO | 1955/08/08 | 65 YEARS | M | 65 YEARS | 2 | CHEST STANDING POSITION SERIAL P→ A | 0.33 | 6.6 |
| 2021/01/05 16:00:53 | 00004 | SATO, JIRO | SATO, JIRO | 1960/04/04 | 60 YEARS | M | 60 YEARS | 1 | CHEST STANDING POSITION SERIAL P→ A | 0.12 | 2.4 |
| 2021/01/05 15:59:33 | 00005 | TAKAHASHI, UMEKO | TAKAHASHI, UMEKO | 1955/05/05 | 65 YEARS | F | 65 YEARS | 1 | CHEST STANDING POSITION SERIAL P→ A | 0.15 | 3.0 |
| 2020/12/25 14:49:25 | 00007 | SHIRO, WATANABE | SHIRO, WATANABE | 1950/07/07 | 70 YEARS | M | 70 YEARS | 1 | CHEST STANDING POSITION SERIAL P→ A | 0.11 | 2.2 |

IMAGING LIST

22c

| IMAGING CONDITIONS 1 | IMAGING DATE AND TIME ▼ | NUMBER OF FRAMES | FPS | TOTAL ESD [mGy] | EQUIVALENT NUMBER INFORMATION |
|---|---|---|---|---|---|
| CHEST STANDING POSITION SERIAL P → A | 2020/12/21 14:00:22 | 100 | 15 | 0.33 | 6.6 |

INFORMATION OUTPUT APPARATUS, INFORMATION PROCESSING APPARATUS, RECORDING MEDIUM, INFORMATION OUTPUT METHOD, AND INFORMATION PROCESSING METHOD

CROSS-REFERENCE TO RELATED APPLICATIONS

The entire disclosure of Japanese Patent Application No. 2023-015757 filed on Feb. 6, 2023 is incorporated herein by reference in its entirety.

BACKGROUND OF THE INVENTION

Technical Field

The present invention relates to an information output apparatus, an information processing apparatus, a recording medium, an information output method, and an information processing method.

Description of Related Art

Conventionally, in simple X-ray imaging, dose management is performed to optimize the amount of radiation exposure. Also in dynamic imaging for obtaining a dynamic image having a plurality of frame images, it is desirable to perform dose management in the same manner as in simple X-ray imaging to optimize the amount of radiation exposure. However, at present, dynamic imaging is a new imaging technique in transition from the stage of clinical research stage to the stage of being used in medical practice, and dose management protocols have not been settled.

In this regard, JP 6860113 B1 discloses that even in the case of a dynamic image with thinned frame images, the dose for all frame images before thinning out the frame images is managed as the dose. Such management can enable more accurate management of the actually exposed dose.

SUMMARY OF THE INVENTION

In a series of X-ray imaging operations such as in dynamic imaging, the number of images to be captured is larger than that in simple X-ray imaging. Therefore, in some cases the patient may be anxious about the amount of radiation exposure from the dynamic imaging, and a technician or doctor may check the actual amount of radiation exposure after a series of X-ray imaging operations.

In such cases, it is necessary for the technician or doctor to explain to the patient the actual amount of radiation exposure from the series of X-ray imaging operations. However, there is a problem in that it is difficult to explain to the patient in an easy-to-understand manner how much the amount of radiation exposure has been.

The present invention has been made in view of the abovementioned problem, and an object of the present invention is to provide an information output apparatus, an information processing apparatus, a recording medium, an information output method, and an information processing method capable of providing dose information for a series of X-ray imaging operations that is easy for a medical site or a patient to understand.

To achieve at least one of the abovementioned objects, according to an aspect of the present invention, an information output apparatus reflecting one aspect of the present invention includes:

a hardware processor that outputs information based on a number of simple X-ray imaging operations as information pertaining to a continuous imaging dose, the continuous imaging dose being a dose in a series of X-ray imaging operations.

To achieve at least one of the abovementioned objects, according to an aspect of the present invention, an information processing apparatus reflecting one aspect of the present invention includes:

a hardware processor that calculates information based on a number of simple X-ray imaging operations as information pertaining to a continuous imaging dose, the continuous imaging dose being a dose in a series of X-ray imaging operations, the information being calculated according to the following formula:

Information based on number of simple X-ray imaging operations=dose in series of X-ray imaging operations/dose per simple X-ray imaging operation.

To achieve at least one of the abovementioned objects, according to an aspect of the present invention, a recording medium reflecting one aspect of the present invention is a non-transitory computer-readable recording medium storing a program that causes a computer of an information output apparatus to:

output information based on a number of simple X-ray imaging operations as information pertaining to a continuous imaging dose, the continuous imaging dose being a dose in a series of X-ray imaging operations.

To achieve at least one of the abovementioned objects, according to an aspect of the present invention, an information output method reflecting one aspect of the present invention includes:

outputting, by a hardware processor, information based on a number of simple X-ray imaging operations as information pertaining to a continuous imaging dose, the continuous imaging dose being a dose in a series of X-ray imaging operations.

To achieve at least one of the abovementioned objects, according to an aspect of the present invention, an information processing method reflecting one aspect of the present invention includes:

calculating, by a hardware processor, information based on a number of simple X-ray imaging operations as information pertaining to a continuous imaging dose, the continuous imaging dose being a dose in a series of X-ray imaging operations, the information being calculated according to the following formula:

Information based on number of simple X-ray imaging operations=dose in series of X-ray imaging operations/dose per simple X-ray imaging operation.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 8 is a flowchart illustrating a flow of a pre-imaging dose information output process according to a second embodiment; and FIG. 9 is a diagram illustrating an example of a display screen according to a third embodiment.

DETAILED DESCRIPTION

Hereinafter, one or more embodiments of the present invention will be described with reference to the drawings. However, the scope of the invention is not limited to the disclosed embodiments.

In the embodiment, dynamic imaging will be described as an example. However, a series of X-ray imaging operations includes fluoroscopic imaging and tomosynthesis or other imaging for generating tomographically reconstructed images from a continuous image of pulsed X-rays.

First Embodiment

1. Radiographic Imaging System

First, a schematic configuration of a radiographic imaging system (hereinafter, imaging system 100) according to the present embodiment will be described.

Figure 1:
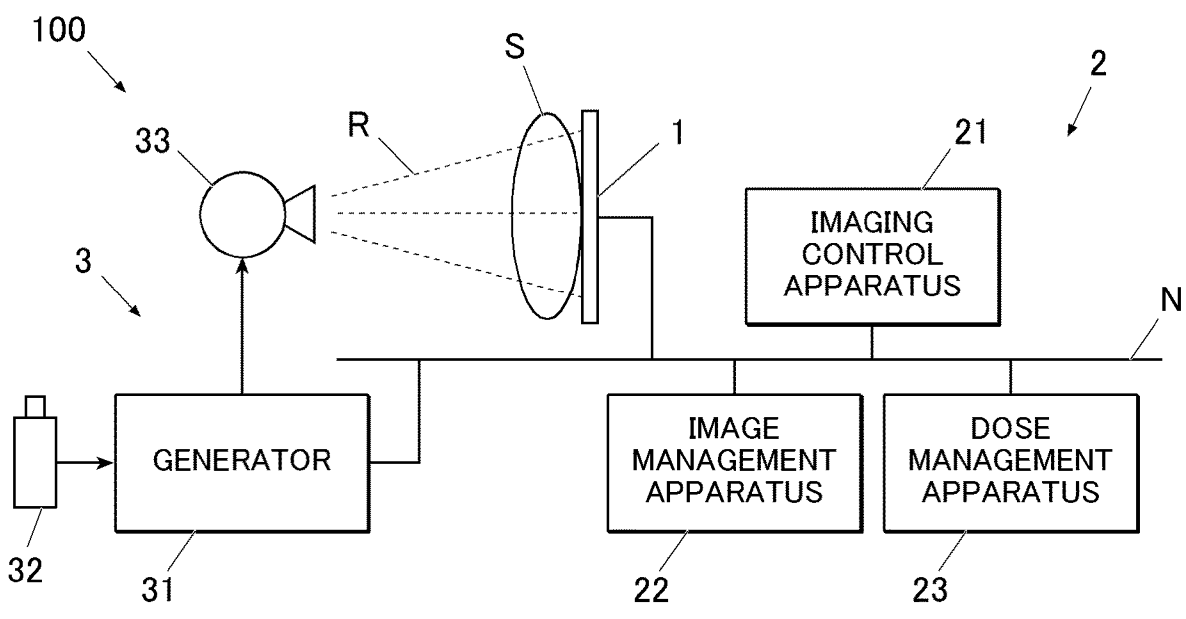
FIG. 1 is a block diagram illustrating a radiographic imaging system according to a first embodiment.

FIG. 1 is a block diagram illustrating the imaging system 100.

As illustrated in FIG. 1, the imaging system 100 includes a radiographic imaging apparatus (hereinafter, imaging apparatus 1), an image management system 2, and a radiation generation apparatus (hereinafter, generation apparatus 3).

The imaging apparatus 1, the image management system 2, and the generation apparatus 3 are capable of communicating with each other via, for example, a communication network N (a local area network (LAN), a wide area network (WAN), the Internet, or the like).

Note that the imaging system 100 may be installed in an imaging room or may be configured to be movable (for example, a medical cart).

The imaging system 100 may be capable of communicating with a hospital information system (HIS), a radiology information system (RIS), or the like (not illustrated).

1-1. Radiation Generation Apparatus

The generation apparatus 3 includes a generator 31, an irradiation instruction switch 32, and a radiation source 33.

The generator 31 applies a voltage corresponding to preset imaging conditions to the radiation source 33 (bulb) on the basis of the irradiation instruction switch 32 being operated.

The imaging conditions include conditions related to a subject S, such as imaging region, imaging direction, body position of the subject S, physique of the subject S, state of the subject S, age of the subject S, and sex of the subject S, for example.

The imaging region is, for example, the chest, a leg, or the like.

The physique of the subject S may be designated by a numerical value such as the weight, height, body mass index (BMI), or body thickness of the subject S, or may be a range-based classification. The range-based classifications are, for example, large/medium/small, thin/average/thick, and the like.

The state of the subject S includes the type of breathing such as breath holding and deep breathing.

The age of the subject S may be designated by a numerical value or may be a range-based classification (child, adult, or the like).

The sex of the subject S may be identified from physical structural characteristics.

The imaging conditions may also include, for example, conditions related to irradiation with radiation R, such as the type of examination, tube voltage and tube current, imaging time, current-time product (mAs value), distance (focus-film distance (FFD) or source image receptor distance (SID)) from the radiation source 33 to the imaging apparatus 1, frame rate, the presence or absence of a grid, the type of additional filter, and the manufacturer and classification of the generation apparatus 3. The frame rate is the number of frames acquired per second.

When a voltage is applied from the generator 31, the radiation source 33 generates radiation R (e.g., X-rays) in a dose corresponding to the applied voltage.

In addition, the generation apparatus 3 generates the radiation R in a mode corresponding to the form (a still image or a dynamic image having a plurality of frame images) of radiographic image to be generated.

In the case of the still image, the emission of the radiation R is performed once per press of the irradiation instruction switch 32.

In the case of the dynamic image, the radiation R is pulsed repeatedly a plurality of times per predetermined time (for example, 15 times per second) or the radiation R is emitted continuously for a predetermined time per press of the irradiation instruction switch 32.

Upon completion of a still imaging operation or a series of X-ray imaging operations, the generation apparatus 3 outputs information about imaging execution conditions, which are the actual imaging conditions under which imaging is performed.

A series of X-ray imaging operations refers to imaging operations from an instruction to start X-ray imaging (for example, a press of the irradiation instruction switch 32) to cancellation of the imaging instruction (for example, a release of the press of the irradiation instruction switch 32).

1-2. Radiographic Imaging Apparatus

The imaging apparatus 1 generates digital data of a radiographic image in which the imaging region of the subject S is captured.

The imaging apparatus 1 is, for example, a portable flat panel detector (FPD) apparatus.

Specifically, although not illustrated in the drawings, the imaging apparatus 1 includes a sensor board, a scanner, a reader, a controller, a communicator, and the like.

On the sensor board, imaging elements that generate electric charges corresponding to the dose in response to receiving the radiation R and switch elements that accumulate and release the electric charges are arranged two dimensionally (in a matrix).

The scanner switches each switch element on/off.

The reader reads the quantity of electric charge released from each pixel as a signal value.

The controller controls each component and generates a radiographic image from the plurality of signal values read by the reader.

The communicator transmits data of the generated radiographic image, various signals, and the like to an external apparatus (the image management system 2, the generation apparatus 3, or the like), and receives various information and various signals from the external apparatus.

The imaging apparatus 1 accumulates and releases electric charges and reads signal values in synchronization with the timing at which the radiation R is emitted from the generation apparatus 3. Accordingly, the imaging apparatus 1 generates still image data, which is image data of a still image, or dynamic image data, which is image data of a dynamic image.

When generating still image data, the imaging apparatus 1 generates a radiographic image only once per press of the irradiation instruction switch 32.

In the case of generating the dynamic image data, the imaging apparatus 1 repeatedly generates frame images forming the dynamic image a plurality of times per predetermined time (for example, 15 times per second) per press of the irradiation instruction switch 32.

Note that the imaging apparatus 1 may be integrated with the generation apparatus 3 (e.g., a computed tomography (CT) apparatus or the like).

Furthermore, the imaging apparatus 1 may cause a display apparatus connected to itself to display the generated dynamic image in real time.

1-3. Image Management System

The image management system 2 includes an imaging control apparatus 21, an image management apparatus 22, and a dose management apparatus 23.

1-3-1. Imaging Control Apparatus

The imaging control apparatus 21 receives still image data and dynamic image data from the imaging apparatus 1.

Further, the imaging control apparatus 21 is configured as a PC, a dedicated apparatus, or the like, and also serves as a console.

That is, the imaging control apparatus 21 has a function of setting various imaging conditions (tube voltage, tube current, irradiation time (mAs value), imaging region, imaging direction, and the like) in at least one of the imaging apparatus 1 and the generation apparatus 3.

The imaging control apparatus 21 sets the imaging conditions on the basis of imaging order information acquired from another system (HIS, RIS, or the like) or an operation performed by a user (such as a technician, for example).

Note that the imaging control apparatus 21 may be separate from the console.

Further, the imaging control apparatus 21 may also serve as an apparatus other than the console.

Figure 2:
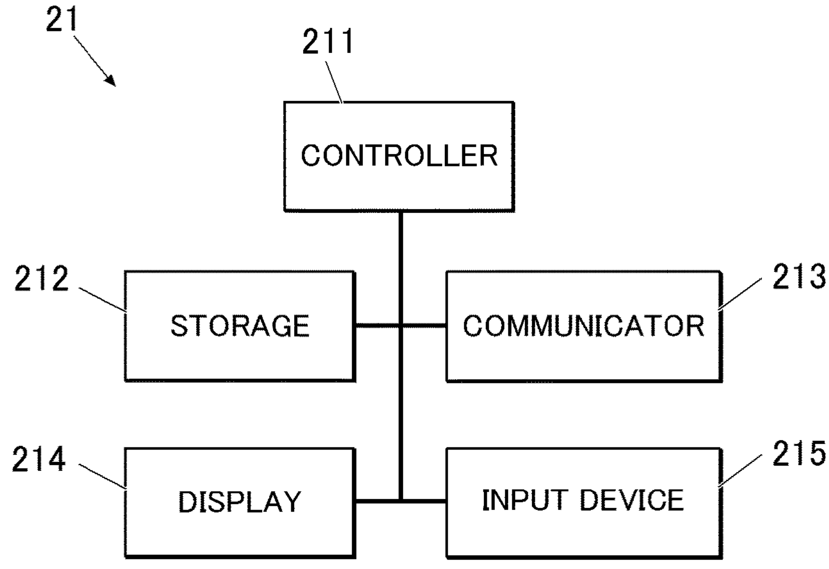
FIG. 2 is a block diagram illustrating an imaging control apparatus according to the first embodiment.

FIG. 2 is a block diagram illustrating the imaging control apparatus 21.

As illustrated in FIG. 2, the imaging control apparatus 21 includes a controller 211 (hardware processor), storage 212, a communicator 213, a display 214, and an input device 215.

The controller 211, the storage 212, the communicator 213, the display 214, and the input device 215 are electrically connected to each other via a bus or the like.

The controller 211 includes a central processing unit (CPU), random access memory (RAM), read-only memory (ROM), and the like.

The ROM stores various programs to be executed by the CPU, parameters necessary for executing the programs, and the like.

The CPU reads out various programs stored in the ROM, loads the programs into the RAM, executes various processes in accordance with the loaded programs, and centrally controls operations by each component of the imaging control apparatus 21.

The storage 212 includes nonvolatile memory, a hard disk, or the like.

The storage 212 stores a reference entrance surface dose (ESD), which is the entrance surface dose per simple X-ray imaging operation. The entrance surface dose is equivalent to the air dose, including scattered rays from the surface of the subject.

The reference ESD is, for example, a reference ESD in simple X-ray imaging used in a facility that performs dynamic imaging (a series of X-ray imaging operations). In other words, in this case, the reference ESD is predetermined for each facility.

The reference ESD is, for example, a value corresponding to the subject. Specifically, the reference ESD is a value corresponding to, for example, the physique of the subject, the age of the subject, the sex of the subject, or the like.

In addition, the reference ESD is preferably a diagnostic reference level for general imaging (simple X-ray imaging).

In Japan, for example, “National Diagnostic Reference Levels in Japan (2020): Japan DRLs 2020, Jul. 3, 2020” are used as diagnostic reference levels. In the United States, for example, “ACR-AAPM-SPR PRACTICE PARAMETER FOR DIAGNOSTIC REFERENCE LEVELS AND ACHIEVABLE DOSES IN MEDICAL X-RAY IMAGING Revised 2018 (Resolution 40)” is used. In Europe, for example, “Lung scan dose” on page 24 of “Radiation Protection 109” is used.

The communicator 213 includes a communication module and the like.

The communicator 213 transmits and receives various signals and various data to and from an external apparatus (the imaging apparatus 1, the image management apparatus 22, the dose management apparatus 23, the generation apparatus 3, and the like) connected in a wired or wireless manner via the communication network N.

The display 214 includes, for example, a liquid crystal display (LCD), an electronic luminescent display (ELD), a cathode ray tube (CRT), or the like.

The display 214 displays a radiographic image or the like corresponding to an image signal received from the controller 211.

The input device 215 includes a keyboard (cursor keys, numeric keys, various function keys, and the like), a pointing device (mouse or the like), a touch screen layered on or under the surface of the display 214, and the like.

The input device 215 outputs to the controller 211 a control signal corresponding to an operation performed by the user.

Note that the imaging control apparatus 21 may also not include the input device 215, and may receive a control signal from an input apparatus provided separately from the imaging control apparatus 21 through, for example, the communicator 213. Further, the imaging control apparatus 21 may also not include the display 214, and may output an image signal to a display apparatus (monitor) provided separately from the imaging control apparatus 21.

In a case where the external apparatus (the image management apparatus 22, the dose management apparatus 23, or the like) includes an input device, the imaging control apparatus 21 may receive a control signal from the input device of the external apparatus. In a case where the external apparatus includes a display, the imaging control apparatus 21 may output an image signal to the display of the external apparatus. In other words, the imaging control apparatus 21 may share the display and the input device with the external apparatus.

1-3-2. Image Management Apparatus

The image management apparatus 22 manages image data (still image data, dynamic image data, and the like) generated by the imaging apparatus 1.

The image management apparatus 22 is a picture archiving and communication system (hereinafter, PACS), an imaging workstation (hereinafter, IWS), or the like.

The image management apparatus 22 may be separate from the PACS or the IWS.

Furthermore, the image management apparatus 22 may also serve as an apparatus other than the PACS or the IWS.

Figure 3:
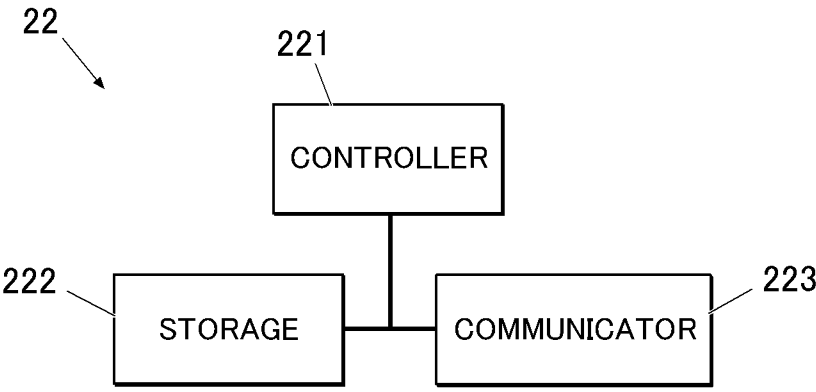
FIG. 3 is a block diagram illustrating an image management apparatus according to the first embodiment.

FIG. 3 is a block diagram illustrating the image management apparatus 22.

As illustrated in FIG. 3, the image management apparatus 22 includes a controller 221, storage 222, and a communicator 223.

The controller 221, the storage 222, and the communicator 223 are electrically connected to each other via a bus or the like.

Note that the image management apparatus 22 may further include a display and an input device.

The controller 221 includes a CPU, RAM, ROM, and the like.

The ROM stores various programs to be executed by the CPU, parameters necessary for executing the programs, and the like.

The CPU reads out various programs stored in the ROM, loads the programs into the RAM, executes various processes in accordance with the loaded programs, and centrally controls operations by each component of the image management apparatus 22.

The storage 222 includes nonvolatile memory, a hard disk, or the like.

In addition, the storage 222 stores image data (still image data, dynamic image data, or the like) generated by the imaging apparatus 1.

Note that the storage 222 may also be capable of storing image data other than image data generated by the imaging apparatus 1.

In addition, the storage 222 stores radiation dose information corresponding to a radiation dose in imaging for obtaining still image data or dynamic image data received from the imaging control apparatus 21.

The communicator 223 includes a communication module and the like.

The communicator 223 transmits and receives various signals and various data to and from an external apparatus (the imaging apparatus 1, the imaging control apparatus 21, and the dose management apparatus 23) connected via the communication network N in a wired or wireless manner.

1-3-3. Dose Management Apparatus

The dose management apparatus 23 manages radiation dose information corresponding to a radiation dose in imaging for obtaining still image data or dynamic image data.

The dose management apparatus 23 is configured as a PC, a dedicated apparatus, a virtual server in the cloud, or the like.

Note that the dose management apparatus 23 may manage radiation dose information corresponding to a radiation dose in a case other than imaging for obtaining still image data or dynamic image data.

Furthermore, the dose management apparatus 23 may be included in the image management apparatus 22.

Figure 4:
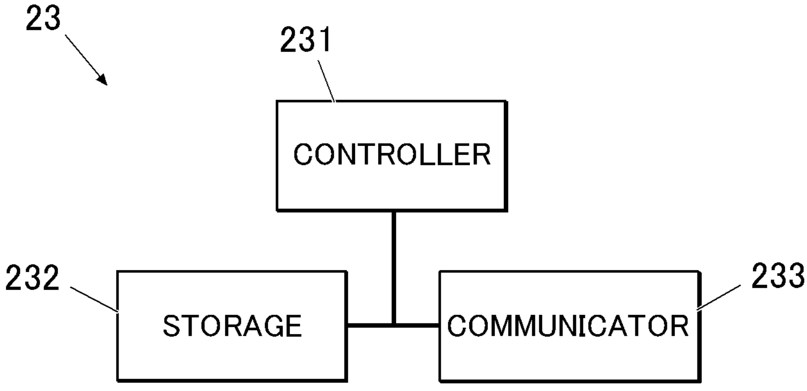
FIG. 4 is a block diagram illustrating a dose management apparatus according to the first embodiment.

FIG. 4 is a block diagram illustrating the dose management apparatus 23.

As illustrated in FIG. 4, the dose management apparatus 23 includes a controller 231, a storage 232, and a communicator 233.

The controller 231, the storage 232, and the communicator 233 are electrically connected to each other via a bus or the like.

Note that the dose management apparatus 23 may further include a display and an input device.

The controller 231 includes a CPU, RAM, ROM, and the like.

The ROM stores various programs to be executed by the CPU, parameters necessary for executing the programs, and the like.

The CPU reads out various programs stored in the ROM, loads the programs into the RAM, executes various processes in accordance with the loaded programs, and centrally controls operations by each component of the dose management apparatus 23.

The storage 232 includes nonvolatile memory, a hard disk, or the like.

In addition, the storage 232 stores radiation dose information corresponding to a radiation dose in imaging for obtaining still image data or dynamic image data received from the imaging control apparatus 21.

Note that the storage 232 may also be capable of storing radiation dose information other than the radiation dose information corresponding to a radiation dose in imaging for obtaining still image data or dynamic image data.

In addition, the storage 232 stores image data (still image data, dynamic image data, or the like) generated by the imaging apparatus 1.

The communicator 233 includes a communication module and the like.

The communicator 233 transmits and receives various signals and various data to and from an external apparatus (the imaging apparatus 1, the imaging control apparatus 21, and the image management apparatus 22) connected in a wired or wireless manner via the communication network N.

2. Operations by Radiographic Imaging System

The imaging system 100 configured as described above operates as follows.

First, the generation apparatus 3 irradiates with radiation R an imaging region of the subject S positioned between the radiation source 33 of the generation apparatus 3 and the imaging apparatus 1, the radiation source 33 and the imaging apparatus 1 being arranged opposite to each other with a gap therebetween.

Then, the imaging apparatus 1 generates a radiographic image (still image, dynamic image) in which the imaging region is captured, and transmits image data (still image data, dynamic image data) thereof to the imaging control apparatus 21.

Upon completion of imaging, the generation apparatus 3 transmits, to the imaging control apparatus 21, information on the imaging execution conditions in the imaging for obtaining the still image data or the dynamic image data.

In the first embodiment, the imaging control apparatus 21 functions as an information processing apparatus and an information output apparatus.

Figure 5:
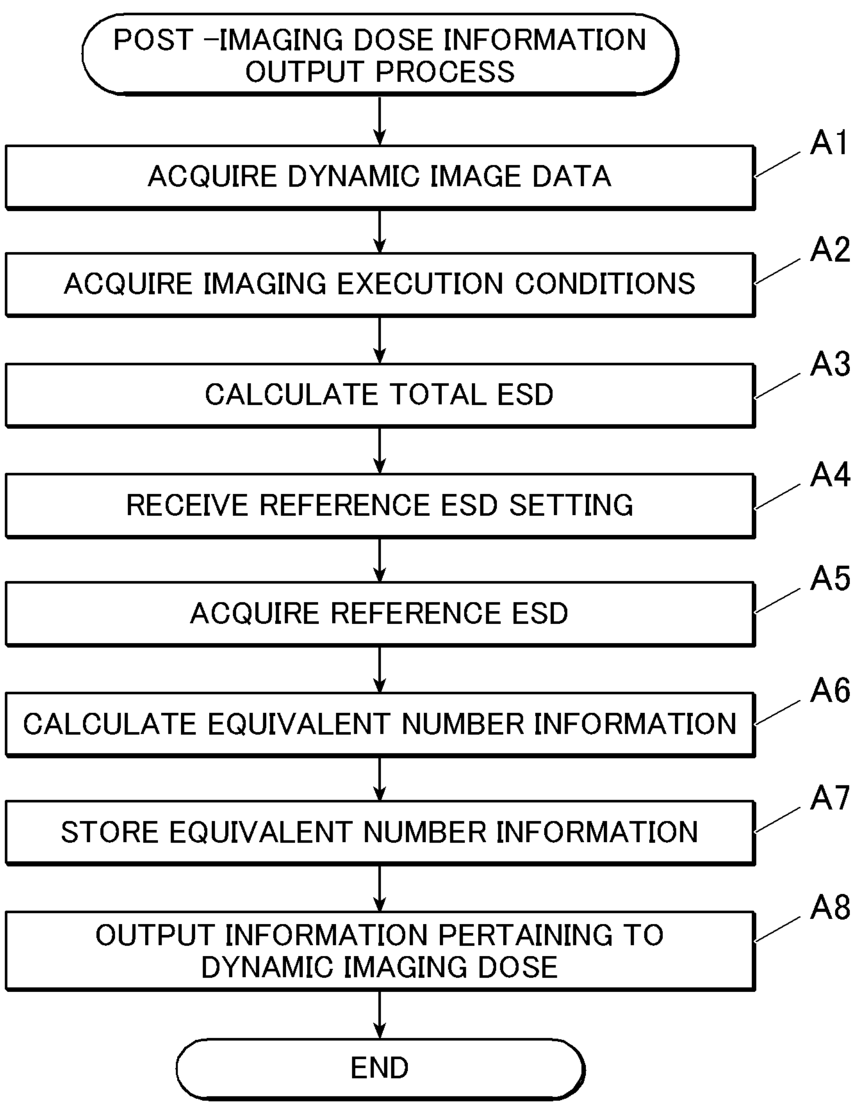
FIG. 5 is a flowchart illustrating a flow of a post-imaging dose information output process according to the first embodiment.

The controller 211 of the imaging control apparatus 21 executes the post-imaging dose information output process illustrated in FIG. 5 when dynamic imaging has been performed in the generation apparatus 3 and the imaging apparatus 1.

In the post-imaging dose information output process, the controller 211 calculates and outputs equivalent number information indicating how many entrance surface doses in simple X-ray imaging are equivalent to the entrance surface dose in a series of dynamic imaging operations.

(Post-Imaging Dose Information Output Process)

First, the controller 211 of the imaging control apparatus 21 receives and acquires dynamic image data in a series of dynamic imaging operations from the imaging apparatus 1 (step A1).

Next, the controller 211 receives and acquires information on imaging execution conditions (actual imaging conditions) in a series of dynamic imaging operations from the generation apparatus 3 (step A2).

Next, the controller 211 calculates the total ESD, which is the entrance surface dose in the series of dynamic imaging operations, on the basis of the information on the imaging execution conditions acquired in step A2 (step A3). That is, the total ESD (entrance surface dose in a series of dynamic imaging operations) is a dose based on the imaging conditions of the subject.

In step A3, the controller 211 calculates the total ESD on the basis of imaging conditions such as, for example, the type of examination, the FFD (or SID), the tube voltage, the current-time product (mAs value), the frame rate, the imaging time, the body position of the subject, the physique of the subject, the state of the subject, the age of the subject, the sex of the subject, the presence or absence of a grid, the type of additional filter, and the manufacturer and classification of the generation apparatus 3.

Next, the controller 211 displays a settings screen 214*a* on the display 214 and accepts the setting of the reference ESD by the user via the input device 215 (step A4).

Figure 6:
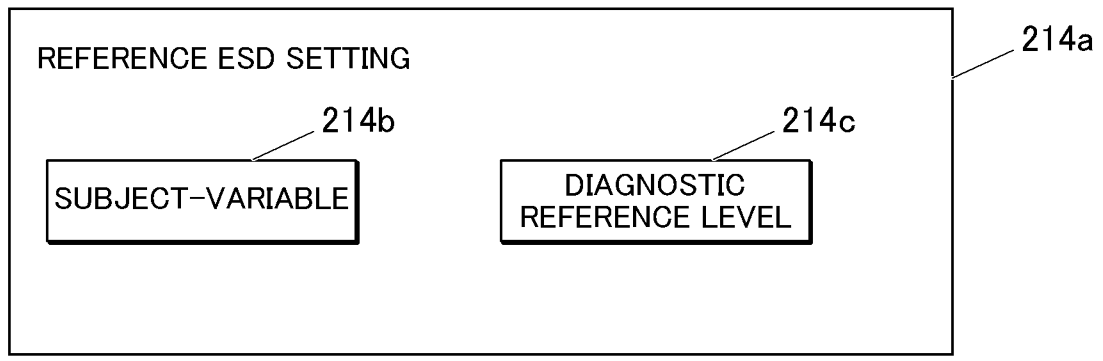
FIG. 6 is a diagram illustrating an example of a settings screen according to the first embodiment.

FIG. 6 illustrates an example of the settings screen 214*a*.

As illustrated in FIG. 6, selection buttons 214*b* and 214*c* are provided on the settings screen 214*a*.

When the selection button 214*b* is selected by the user, the controller 211 sets the reference ESD to a subject-variable type.

Furthermore, when the selection button 214*c* is selected by the user, the controller 211 sets the reference ESD to a diagnostic reference level type.

Next, the controller 211 acquires the reference ESD from the storage 212 on the basis of the setting of the reference ESD received in step A4 (step A5).

To be specific, when the reference ESD is set to the subject-variable type, the controller 211 acquires the reference ESD corresponding to the conditions related to the subject included in the imaging execution conditions acquired in step A2. For example, the controller 211 acquires the reference ESD corresponding to the physique of the subject, the age of the subject, the sex of the subject, and the like.

When the reference ESD is set to the diagnostic reference level type, the controller 211 acquires the diagnostic reference level as the reference ESD. The diagnostic reference level may be, for example, a value corresponding to the conditions related to the subject (such as the age of the subject) included in the imaging execution conditions acquired in step A2.

Next, the controller 211 calculates the equivalent number information (step A6). Here, the controller 211 functions as a calculator. Step A6 is a calculating step.

The equivalent number information is information indicating how many instances of the reference ESD are equivalent to the total ESD, and is calculated by the following formula:

Equivalent number information=dose (total ESD) in series of dynamic imaging operations (series of X-ray imaging operations)/dose (reference ESD) per simple X-ray imaging operation The equivalent number information is information based on the number of simple X-ray imaging operations.

Next, the controller 211 associates the equivalent number information calculated in step A6 with the dynamic image acquired in step A1, and stores the information in the storage 212 (step A7).

That is, the controller 211 associates the dynamic image (series of X-ray images) acquired by the series of dynamic imaging operations (series of continuous imaging operations) with the information (here, the equivalent number information) pertaining to the dynamic imaging dose (information pertaining to the continuous imaging dose). Here, the controller 211 functions as an associator.

Note that in step A7, the controller 211 may store the total ESD and the reference ESD, in addition to the equivalent number information, in association with the dynamic image data.

Whether to store only the equivalent number information in association with the dynamic image data or to store the equivalent number information, the total ESD, and the reference ESD in association with the dynamic image data may be selectable.

Furthermore, the controller 211 may further store information on whether the reference ESD has been set to the subject-variable type or the diagnostic reference level type in association with the dynamic image data.

In addition, in a case where the reference ESD is set to the subject-variable type, the controller 211 may further store conditions related to the subject included in the imaging execution conditions acquired in step A2 in association with the dynamic image data. The conditions related to the subject are the physique of the subject, the age of the subject, the sex of the subject, and the like.

Next, the controller 211 displays and outputs the display screen 214*d* (see FIG. 7) including information pertaining to the dynamic imaging dose on the display 214 (step A8), and ends the process.

The information pertaining to the dynamic imaging dose includes the equivalent number information and the total ESD.

That is, the controller 211 outputs information based on the number of simple X-ray imaging operations as information pertaining to the dynamic imaging dose (continuous imaging dose), which is a dose in a series of dynamic imaging operations (series of X-ray imaging operations). Here, the controller 211 functions as an outputter.

Step A8 is an outputting step.

Figure 7:
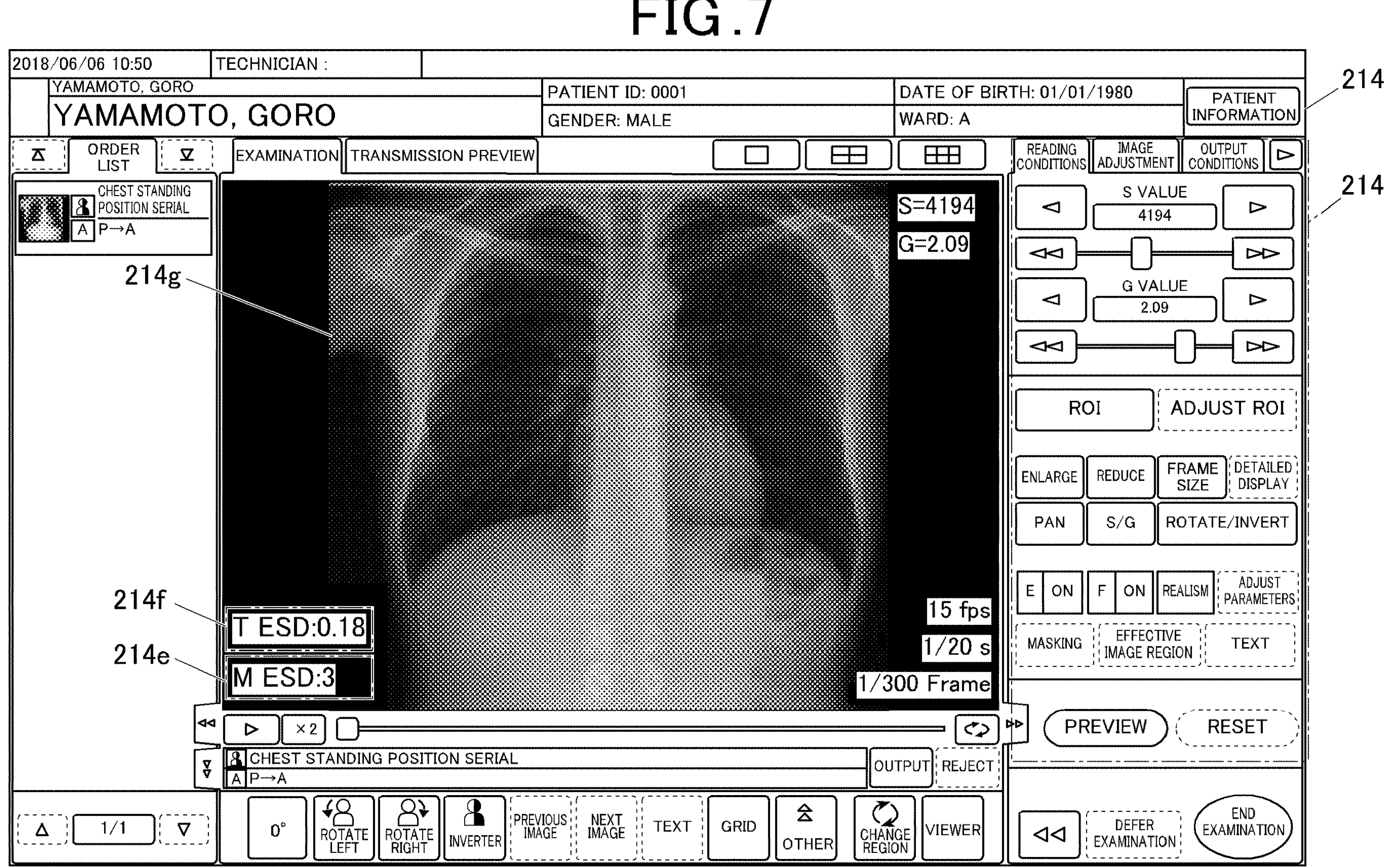
FIG. 7 is a diagram illustrating an example of a display screen according to the first embodiment.

For example, as illustrated in FIG. 7, the controller 211 displays "M ESD: 3" as equivalent number information 214*e* on the display screen 214*d*. This indicates that the total ESD is equivalent to three instances of the reference ESD.

Furthermore, the controller 211 displays, for example, "T ESD: 0.18" as a total ESD 214*f* on the display screen 214*d*. This indicates that the total ESD is 0.18 [mGy].

Furthermore, for example, the controller 211 displays on the display screen 214*d* a frame image 214*g* of the dynamic image data with which the equivalent number information is associated in step A7.

Note that since the equivalent number information and the total ESD are values for a series of dynamic imaging operations, the same value is displayed for each frame image of the dynamic image data with which the equivalent number information is associated in step A7.

In addition, as illustrated in FIG. 7, the controller 211 may display the equivalent number information 214*e* and the total ESD 214*f* in the form of an overlay on the frame image 214*g*, or in a control panel portion 214*h* of the display screen 214*d*.

Furthermore, the notation method for the equivalent number information 214*e* and the total ESD 214*f* is not limited to the example illustrated in FIG. 7, and another notation may be used.

The controller 211 may further display the reference ESD on the display screen 214*d*.

Furthermore, the controller 211 may further display, on the display screen 214*d*, information indicating whether the reference ESD has been set to the subject-variable type or to the diagnostic reference level type.

Furthermore, when the reference ESD is set to the subject-variable type, the controller 211 may further display, on the display screen 214*d*, conditions related to the subject included in the imaging execution conditions acquired in step A2.

Furthermore, the controller 211 may display, on the display screen 214*d*, a comparison between the equivalent number information for the case where the reference ESD is set to the subject-variable type and the equivalent number information for the case where the reference ESD is set to the diagnostic reference level type.

Whether the reference ESD is set to the subject-variable type or the diagnostic reference level type may be selectable for each facility, clinical department (requesting department), part of the body, or user.

Second Embodiment

Next, a second embodiment of the present invention will be described. Note that in the second embodiment, the same components as those of the above-described embodiment are denoted by the same reference numerals, and description thereof will be omitted.

In the second embodiment, the imaging control apparatus 21 functions as an information processing apparatus and an information output apparatus as in the first embodiment.

The controller 211 of the imaging control apparatus 21 executes the pre-imaging dose information output process illustrated in FIG. 8 before the dynamic imaging is performed in the generation apparatus 3 and the imaging apparatus 1.

(Pre-Imaging Dose Information Output Process)

First, the controller 211 of the imaging control apparatus 21 acquires information on scheduled imaging conditions (imaging conditions at the time of planning an examination including imaging) in a series of dynamic imaging operations (step B1).

Specifically, the controller 211 acquires the information on scheduled imaging conditions from imaging order information acquired from another system (HIS, RIS, or the like) or an operation performed by a user (such as a technician, for example).

Next, the controller 211 calculates the total ESD, which is the entrance surface dose in the series of dynamic imaging operations, on the basis of the information on the scheduled imaging conditions acquired in step B1 (step B2).

In step B2, the controller 211 calculates the total ESD on the basis of scheduled imaging conditions such as, for example, the type of examination, the FFD (or SID), the tube voltage, the current-time product (mAs value), the frame rate, the imaging time, the body position of the subject, the physique of the subject, the state of the subject, the age of the subject, the sex of the subject, the presence or absence of a grid, the type of additional filter, and the manufacturer and classification of the generation apparatus 3.

Next, the controller 211 executes step B3, which is similar to the above-described post-imaging dose information output process step A4.

Next, the controller 211 acquires the reference ESD from the storage 212 on the basis of the setting of the reference ESD received in step B3 (step B4).

To be specific, when the reference ESD is set to the subject-variable type, the controller 211 acquires the reference ESD corresponding to the conditions related to the subject included in the scheduled imaging conditions acquired in step B1. For example, the controller 211 acquires the reference ESD corresponding to the physique of the subject, the age of the subject, the sex of the subject, and the like.

When the reference ESD is set to the diagnostic reference level type, the controller 211 acquires the diagnostic reference level as the reference ESD. The diagnostic reference level may be, for example, a value corresponding to the conditions related to the subject (such as the age of the subject) included in the scheduled imaging conditions acquired in step B1.

Next, the controller 211 executes step B5, which is similar to the above-described post-imaging dose information output process step A6. Step B5 is a calculating step.

Next, the controller 211 stores the equivalent number information calculated in step B5 in the storage 212 (step B6).

Note that in step B6, the controller 211 may store the total ESD and the reference ESD in addition to the equivalent number information.

Furthermore, whether to store only the equivalent number information or to store the equivalent number information, the total ESD, and the reference ESD may be selectable.

Furthermore, the controller 211 may further store information indicating whether the reference ESD has been set to the subject-variable type or the diagnostic reference level type.

Furthermore, when the reference ESD is set to the subject-variable type, the controller 211 may further store conditions related to the subject included in the scheduled imaging conditions acquired in step B1. The conditions related to the subject are the physique of the subject, the age of the subject, the sex of the subject, and the like.

Next, the controller 211 performs step B7, which is similar to the above-described post-imaging dose information output processing step A8, on the display 214, and ends the process.

Step B7 is an outputting step.

Note that when any of the scheduled imaging conditions are changed by the user, the controller 211 may calculate equivalent number information before and after the change and display a comparison on the display screen 214*d*.

Accordingly, the user (such as a technician, for example) can consider the change of the imaging conditions more appropriately.

Furthermore, in addition to executing the pre-imaging dose information output process before dynamic imaging is performed, the controller 211 may execute the post-imaging dose information output process after dynamic imaging is performed. In this case, the controller 211 may display, on the display screen 214*d*, a comparison between the equivalent number information based on the scheduled imaging conditions and the equivalent number information based on the imaging execution conditions.

As an example, a case will be described in which "frame rate: 15 [fps], imaging time: 3 [s]" is set as the scheduled imaging conditions, but imaging is actually performed with the imaging execution conditions set to "frame rate: 15 [fps], imaging time: 1.8 [s]". In this case, displaying a comparison between the equivalent number information based on the scheduled imaging conditions and the equivalent number information based on the imaging execution conditions makes it possible to explain to the subject (patient) in an easily understood way that the radiation dose (entrance surface dose) has been reduced from the originally scheduled dose.

As another example, a case will be described in which "physique of subject: large" is set as the scheduled imaging conditions, but estimating the physique from a captured image returns a result different from "physique of subject: large", that is, the imaging execution conditions are not "physique of subject: large". In this case, displaying a comparison between the equivalent number information based on the scheduled imaging conditions and the equivalent number information based on the imaging execution conditions makes it possible to recognize that the scheduled imaging conditions and the imaging execution conditions are different.

Further, the controller 211 may execute the post-imaging dose information output process at the next timing. Specifically, the timing is when dynamic imaging is performed in the generation apparatus 3 and the imaging apparatus 1, and the controller 211 has received dynamic image data in the dynamic imaging from the imaging apparatus 1 but has not received information on imaging execution conditions in the dynamic imaging from the generation apparatus 3.

This is, for example, a case where the generation apparatus 3 and the imaging control apparatus 21 are independent of each other (retrofit), and a time lag occurs from when the generation apparatus 3 transmits the information on the imaging execution conditions to when the controller 211 receives the information.

In this case, in the post-imaging dose information outputting step A2, the controller 211 acquires information on the scheduled imaging conditions in the series of dynamic imaging operations.

Next, in step A3, the controller 211 acquires part of the information on the imaging execution conditions from the dynamic image data acquired in step A1. The imaging execution conditions which can be acquired from the dynamic image data are, for example, the imaging time, the physique of the subject, and the like.

Then, the controller 211 acquires, from the scheduled imaging conditions acquired in step A2, imaging conditions that cannot be acquired from the dynamic image data.

Next, the controller 211 calculates the total ESD in the series of dynamic imaging processes on the basis of part of the information on the imaging execution conditions and part of the information on the scheduled imaging conditions acquired from the dynamic image data acquired in step A1.

Then, in step A5, the controller 211 executes the following processing.

To be specific, when the reference ESD is set to the subject-variable type, the controller 211 acquires the reference ESD corresponding to the imaging execution conditions acquired from the dynamic image data acquired in step A1 or the conditions related to the subject included in the scheduled imaging conditions acquired in step A2. For example, the controller 211 acquires the reference ESD corresponding to the physique of the subject, the age of the subject, the sex of the subject, and the like.

When the reference ESD is set to the diagnostic reference level type, the controller 211 acquires the diagnostic reference level as the reference ESD. The diagnostic reference level may be, for example, a value corresponding to the imaging execution conditions acquired from the dynamic image data acquired in step A1 or conditions related to the subject (such as the age of the subject) included in the scheduled imaging conditions acquired in step A2.

Then, in step A8, when displaying the information (including the equivalent number information and the total ESD) pertaining to the dynamic imaging dose, the controller 211 presents a display like the following, for example.

To be specific, the controller 211 displays, for example, "M ESD: 3 (provisional)" as the equivalent number information 214*e* on the display screen 214*d*.

In addition, for example, the controller 211 displays "T ESD: 0.18 (provisional)" as the total ESD 214*f* on the display screen 214*d*.

A case will be described in which the controller 211 executes the pre-imaging dose information output process before dynamic imaging is performed, executes the post-imaging dose information output process after dynamic imaging is performed and before the information on the imaging execution conditions is received, and further executes the post-imaging dose information output process again after the information on the imaging execution conditions is received.

In this case, before the dynamic imaging is performed, the controller 211 displays, on the display screen 214*d*, information (including equivalent number information and total ESD) pertaining to the dynamic imaging dose based on the information about the scheduled imaging conditions.

During the dynamic imaging, the controller 211 does not display information pertaining to the dynamic imaging dose on the display screen 214*d*.

After the dynamic imaging is performed and before the information on the imaging execution conditions is received, the controller 211 displays, on the display screen 214*d*, part of the information on the imaging execution conditions acquired from the dynamic image data and information pertaining to the dynamic imaging dose based on part of the information on the scheduled imaging conditions.

Next, after the dynamic imaging is performed and the information on the imaging execution conditions is received, the controller 211 displays, on the display screen 214*d*, information pertaining to the dynamic imaging dose based on the imaging execution conditions.

Third Embodiment

Next, a third embodiment of the present invention will be described. Note that in the third embodiment, the same components as those of the above-described embodiments are denoted by the same reference numerals, and description thereof will be omitted.

In the third embodiment, the image management apparatus 22 or the dose management apparatus 23 functions as an information processing apparatus and an information output apparatus.

In this case, the image management apparatus 22 (or the dose management apparatus 23) includes a display and an input device.

Further, the storage 222 (or the storage 232) stores the reference ESD.

The controller 221 (or the controller 231) executes the pre-imaging dose information output process before dynamic imaging is performed in the generation apparatus 3 and the imaging apparatus 1. Alternatively, the controller 221 (or the controller 231) executes the post-imaging dose information output process when the dynamic imaging has been performed in the generation apparatus 3 and the imaging apparatus 1. Alternatively, the controller 221 (or the controller 231) executes both the pre-imaging dose information output process and the post-imaging dose information output process.

That is, the controller 221 (or the controller 231) uses the formula below to calculate information (equivalent number information) based on a number of simple X-ray imaging operations as information pertaining to the dynamic imaging dose (continuous imaging dose), which is a dose in a series of dynamic imaging operations (series of X-ray imaging operations). Here, the controller 221 (or the controller 231) functions as a calculator.

Information based on number of simple X-ray imaging operations=dose (total ESD) in series of dynamic imaging operations (series of X-ray imaging operations)/dose (reference ESD) per simple X-ray imaging operation That is, the controller 221 (or the controller 231) associates the dynamic image (series of X-ray images) acquired by the series of dynamic imaging operations (series of continuous imaging operations) with information pertaining to the dynamic imaging dose (continuous imaging dose). Here, the controller 221 (or the controller 231) functions as an associator.

That is, the controller 221 (or the controller 231) outputs information based on the number of simple X-ray imaging operations as information pertaining to the dynamic imaging dose (continuous imaging dose), which is a dose in a series of dynamic imaging operations (series of X-ray imaging operations). Here, the controller 221 (or the controller 231) functions as an outputter.

The controller 221 (or the controller 231) acquires scheduled imaging conditions from the imaging control apparatus 21 in the pre-imaging dose information output process. Then, the controller 221 (or the controller 231) acquires imaging execution conditions and the dynamic image data from the imaging control apparatus 21 in the post-imaging dose information output process.

Further, the controller 221 (or the controller 231) may display a display screen 22*a* (see FIG. 9) on the display in the post-imaging dose information output process step A8 and/or the pre-imaging dose information output process step B7.

The controller 221 (or the controller 231) displays, on the display screen 22*a*, an examination list 22*b* that is a list of examinations including dynamic imaging, an imaging list 22*c* that is a list of dynamic imagings in one examination, and the like.

The controller 221 (or the controller 231) displays, in the examination list 22*b*, an examination date and time, patient ID, patient name, date of birth, patient age, sex, examination age, that is, the age at the time of examination, the number of (dynamic) imagings, an imaging description (imaging region, body position, and the like), a total ESD aggregate value, an equivalent number information aggregate value, and the like for each of respective examinations.

The total ESD aggregate value is the aggregate value of the total ESD for all dynamic imagings in one examination.

The equivalent number information aggregate value is the aggregate value of the equivalent number information for all dynamic imagings in one examination.

When the user selects one of the examinations in the examination list 22*b*, the controller 221 (or the controller 231) displays, in the imaging list 22*c*, a list of dynamic imagings in the selected examination.

The controller 221 (or the controller 231) displays, in the imaging list 22*c*, the imaging conditions (imaging region, body position, and the like), imaging date and time, number of frames, frame rate (FPS), total ESD, equivalent number information, and the like for each imaging.

Note that the controller 221 (or the controller 231) may display the examination list 22*b* and the imaging list 22*c* on the display screen 22*a* for each subject (patient).

Fourth Embodiment

Next, a fourth embodiment of the present invention will be described. Note that in the fourth embodiment, the same components as those of the above-described embodiments are denoted by the same reference numerals, and description thereof will be omitted.

In the fourth embodiment, the imaging control apparatus 21 functions as an information processing apparatus.

Furthermore, the image management apparatus 22 (or the dose management apparatus 23) functions as an information output apparatus.

In this case, the image management apparatus 22 (or the dose management apparatus 23) includes a display.

In the fourth embodiment, the controller 211 of the imaging control apparatus 21 executes the pre-imaging dose information output process. That is, the controller 211 functions as a calculator.

Additionally, in the pre-imaging dose information output process step B7, the controller 211 transmits and outputs information pertaining to the dynamic imaging dose to the image management apparatus 22 (or the dose management apparatus 23).

Further, the controller 211 of the imaging control apparatus 21 executes the post-imaging dose information output process. That is, the controller 211 functions as a calculator.

Additionally, in the post-imaging dose information outputting process step A8, the controller 211 transmits and outputs information pertaining to the dynamic imaging dose to the image management apparatus 22 (or the dose management apparatus 23).

Then, the controller 221 (or the controller 231) displays information pertaining to the dynamic imaging dose received from the imaging control apparatus 21 on the display.

That is, the controller 221 (or the controller 231) outputs information based on the number of simple X-ray imaging operations as information pertaining to the dynamic imaging dose (continuous imaging dose), which is a dose in a series of dynamic imaging operations (series of X-ray imaging operations). Here, the controller 221 (or the controller 231) functions as an outputter.

Note that in the post-imaging dose information output process step A8, the controller 211 may transmit, to the image management apparatus 22 (or the dose management apparatus 23), information pertaining to the dynamic imaging dose together with dynamic image data associated with the information pertaining to the dynamic imaging dose.

In this way, when dynamic image data and information pertaining to the dynamic imaging dose are outputted together, the information pertaining to the dynamic imaging dose can be output by being written in the header of a DICOM image file of the dynamic image. Output may also be performed using the Grayscale Softcopy Presentation State (GSPS) of the DICOM standard.

Further, in the post-imaging dose information output process step A8, the controller 211 transmits the dynamic image data acquired in step A1 to the image management apparatus 22. The controller 211 may also transmit information pertaining to the dynamic imaging dose to the dose management apparatus 23.

A case will be described in which the imaging system 100 is communicatively connected to an RIS or an electronic medical record system. In this case, in the post-imaging dose information output process step A8, the controller 211 transmits the dynamic image acquired in step A1 to the image management apparatus 22. The controller 211 may also transmit information pertaining to the dynamic imaging dose to the RIS or the electronic medical record system.

In this way, when dynamic image data and information pertaining to the dynamic imaging dose are outputted (transmitted) separately, GSPS or the Radiation Dose Structured Report (RDSR) is used in the case of the DICOM standard. In addition, the transmission may be performed through coordination of a general-purpose file such as an Extensible Markup Language (XML) file.

3. Effects

As described above, the information output apparatus (imaging control apparatus 21, image management apparatus 22, or dose management apparatus 23) of the present embodiment includes an outputter (controller 211, controller 221, or controller 231) that outputs information (equivalent number information) based on a number of simple X-ray imaging operations as information pertaining to a continuous imaging dose (dynamic imaging dose), which is a dose in a series of X-ray imaging operations (series of dynamic imaging operations).

This makes it possible to provide information pertaining to the dynamic imaging dose as information that can be easily understood by a medical site or a patient.

The information output apparatus (imaging control apparatus 21, image management apparatus 22, or dose management apparatus 23) of the present embodiment includes a calculator (controller 211, controller 221, or controller 231) that uses the formula below to calculate information (equivalent number information) based on a number of simple X-ray imaging operations.

Information (equivalent number information) based on number of simple X-ray imaging operations=dose (total ESD) in series of X-ray imaging operations/dose (reference ESD) per simple X-ray imaging operation Thus, it is possible to calculate and output information indicating how many doses (entrance surface doses) in simple X-ray imaging are equivalent to the dynamic imaging dose (entrance surface dose) in a series of X-ray imaging operations (dynamic imaging operations).

Further, in the information output apparatus (imaging control apparatus 21, image management apparatus 22, or dose management apparatus 23) of the present embodiment, the dose per simple X-ray imaging operation is a reference entrance surface dose (ESD) in simple X-ray imaging used in a facility where a series of X-ray imaging operations are performed.

Accordingly, it is possible to calculate and output information pertaining to the dynamic imaging dose according to the reference ESD for each facility.

In the information output apparatus (the imaging control apparatus 21, the image management apparatus 22, or the dose management apparatus 23) of the present embodiment, the dose per simple X-ray imaging operation is a dose corresponding to the subject.

Accordingly, information pertaining to the dynamic imaging dose corresponding to the subject can be calculated and output.

In the information output apparatus (the imaging control apparatus 21, the image management apparatus 22, or the dose management apparatus 23) of the present embodiment, the dose per simple X-ray imaging operation is a diagnostic reference level for general imaging.

Accordingly, information pertaining to the dynamic imaging dose based on the diagnostic reference level for general imaging can be calculated and output.

In the information output apparatus (the imaging control apparatus 21, the image management apparatus 22, or the dose management apparatus 23) of the present embodiment, the continuous imaging dose is a dose based on the imaging conditions of the subject.

Accordingly, the dynamic imaging dose can be easily calculated on the basis of the imaging conditions of the subject.

In the information output apparatus (the imaging control apparatus 21, the image management apparatus 22, or the dose management apparatus 23) of the present embodiment, the imaging conditions of the subject include at least one of the body position of the subject, the body thickness of the subject, the state of the subject, and the type of examination.

Accordingly, the dynamic imaging dose can be easily calculated on the basis of the body position of the subject, the body thickness of the subject, the state of the subject, the type of examination, and the like.

In the information output apparatus (the imaging control apparatus 21, the image management apparatus 22, or the dose management apparatus 23) according to the present embodiment, the outputter (the controller 211, the controller 221, or the controller 231) outputs, as information pertaining to the continuous imaging dose, information based on a number of simple X-ray imaging operations and the continuous imaging dose.

Accordingly, information (equivalent number information) based on a number of simple X-ray imaging operations and the dynamic imaging dose (total ESD) in a series of dynamic imaging operations can be displayed for comparison.

In addition, the information output apparatus (the imaging control apparatus 21, the image management apparatus 22, or the dose management apparatus 23) of the present embodiment includes an associator (the controller 211, the controller 221, or the controller 231) that associates a series of X-ray images (series of dynamic images) acquired by a series of continuous imaging operations with information pertaining to the continuous imaging dose.

Accordingly, a dynamic image acquired by the series of dynamic imaging operations can be managed in association with information (equivalent number information) based on a number of simple X-ray imaging operations and/or the dynamic imaging dose (total ESD) in the series of dynamic imaging operations.

Further, the information processing apparatus (the imaging control apparatus 21, the image management apparatus 22, or the dose management apparatus 23) of the present embodiment includes a calculator (the controller 211, the controller 221, or the controller 231) that uses the formula below to calculate information (equivalent number information) based on a number of simple X-ray imaging operations as information pertaining to the continuous imaging dose, which is a dose in a series of X-ray imaging operations.

Information (equivalent number information) based on number of simple X-ray imaging operations=dose (total ESD) in series of X-ray imaging operations/dose (reference ESD) per simple X-ray imaging operation Thus, it is possible to calculate information indicating how many doses (entrance surface doses) in simple X-ray imaging are equivalent to the dynamic imaging dose (entrance surface dose) in a series of dynamic imaging operations.

4. Other

Although the present invention has been described based on the above embodiments, the description in the above embodiments is of preferred examples of the radiographic imaging system according to the present invention, and the present invention is not limited thereto.

For example, an upper limit value may be set for the cumulative value in the equivalent number information per a predetermined period (for example, one month) for the subject. The predetermined period may be 15 days, half a year, or the like, or may be set for each facility in which the imaging system 100 is installed.

In this case, the storage 212 (or the storage 222 or the storage 232) stores the upper limit.

Then, when the controller 211 (or the controller 221 or the controller 231) executes the pre-imaging dose information output process or the post-imaging dose information output process, the controller calculates the cumulative value in the equivalent number information per the predetermined period for the subject. Additionally, in a case where the difference between the calculated cumulative value and the upper limit value is equal to or less than a predetermined threshold value, that is, in a case where the cumulative value and the upper limit value are close to each other to some extent, the controller 211 (or the controller 221 or the controller 231) performs the following process. The threshold value is preset by a user (e.g., a technician or a doctor).

Specifically, the controller 211 (or the controller 221 or the controller 231) issues a warning by displaying, on the display, an indication that the difference between the cumulative value and the upper limit value is equal to or less than the predetermined threshold value.

The controller 211 (or the controller 221 or the controller 231) may also display, on the display, how many more times dynamic imaging can be performed until the upper limit is reached, or dynamic imaging equivalent to how many simple X-ray imaging operations can be performed until the upper limit is reached, based on the difference between the cumulative value and the upper limit. In this case, the controller 211 (or the controller 221 or the controller 231) calculates, for example, how many more times dynamic imaging can be performed until the upper limit is reached from the total ESD based on the imaging execution conditions of the most recently performed dynamic imaging. Further, for example, the controller 211 (or the controller 221 or the controller 231) calculates the dynamic imaging equivalent to how many more the simple X-ray imaging operations can be performed until the upper limit is reached from the equivalent number information based on the imaging execution conditions of the most recently performed dynamic imaging.

The controller 211 (or the controller 221 or the controller 231) may also add up imaging number information for still imaging and equivalent number information for dynamic imaging, and display the result on the display as a value indicative of the total dose of the subject.

Note that the controller 211 (or the controller 221 or the controller 231) may display the imaging number information for still imaging and the equivalent number information for dynamic imaging separately on the display without adding them together.

Furthermore, although the imaging control apparatus 21, the image management apparatus 22, or the dose management apparatus 23 functions as an information output apparatus in the above embodiments, the configuration is not limited thereto. An external apparatus having a display and communicatively connected via the communication network N may also function as an information output apparatus.

In this case, the imaging control apparatus 21, the image management apparatus 22, or the dose management apparatus 23 transmits information pertaining to the dynamic imaging dose (the equivalent number information and/or the total ESD) to the external apparatus. Then, the external apparatus displays the received information pertaining to the dynamic imaging dose on the display.

Further, the above description discloses an example of using a hard disk, a semiconductor nonvolatile memory, or the like as a computer-readable medium of a program according to the present invention, but the present invention is not limited to this example. Other applicable computer-readable media include portable recording media such as CD-ROM. Furthermore, a carrier wave is also applied as a medium for providing data of a program according to the present invention via a communication line.

Although embodiments of the present invention have been described and illustrated in detail, the disclosed embodiments are made for purposes of illustration and example only and not limitation. The scope of the present invention should be interpreted by terms of the appended claims.

What is claimed is:

1. An information output apparatus comprising:

a hardware processor that obtains imaging execution conditions from a radiation generation apparatus regarding a series of X-ray imaging operations;

determines a continuous imaging dose in the series of X-ray imaging operations;

outputs information based on a number of simple X-ray imaging operations as information pertaining to the continuous imaging dose, the continuous imaging dose being a dose in a series of X-ray imaging operations;

stores a cumulative value of the number of simple X-ray imaging operations per a predetermined period for the subject in a storage of the information output apparatus;

stores an upper limit value for the cumulative value; and issues a warning indicating how many more times the series of X-ray imaging operations can be performed or how many more the simple X-ray imaging operations can be performed until the upper limit is reached based on the imaging execution conditions of the series of X-ray imaging operations.

2. The information output apparatus according to claim 1, wherein the hardware processor calculates the information based on the number of simple X-ray imaging operations according to the following formula:

Information based on number of simple X-ray imaging operations=dose in series of X-ray imaging operations/dose per simple X-ray imaging operation.

3. The information output apparatus according to claim 2, wherein the dose per simple X-ray imaging operation is a reference entrance surface dose (ESD) in simple X-ray imaging used in a facility where a series of X-ray imaging operations are performed.

4. The information output apparatus according to claim 2, wherein the dose per simple X-ray imaging operation is a dose corresponding to a subject.

5. The information output apparatus according to claim 2, wherein the dose per simple X-ray imaging operation is a diagnostic reference level for general imaging.

6. The information output apparatus according to claim 2, wherein the continuous imaging dose is a dose based on imaging conditions of a subject.

7. The information output apparatus according to claim 6, wherein the imaging conditions of a subject include at least one of a body position of the subject, a body thickness of the subject, a state of the subject, and a type of examination.

8. The information output apparatus according to claim 1, wherein the hardware processor outputs the information based on a number of simple X-ray imaging operations and the continuous imaging dose as the information pertaining to the continuous imaging dose.

9. The information output apparatus according to claim 1, wherein the hardware processor associates a series of X-ray images acquired by the series of X-ray imaging operations with the information pertaining to the continuous imaging dose.

10. An information processing apparatus comprising:

a hardware processor that obtains imaging execution conditions from a radiation generation apparatus regarding a series of X-ray imaging operations;

determines a continuous imaging dose in the series of X-ray imaging operations;

calculates information based on a number of simple X-ray imaging operations as information pertaining to continuous imaging dose, the continuous imaging dose being a dose in a series of X-ray imaging operations, the information being calculated according to the following formula:

Information based on number of simple X-ray imaging operations=dose in series of X-ray imaging operations/dose per simple X-ray imaging operation, stores a cumulative value of the number of simple X-ray imaging operations per a predetermined period for the subject in a storage of the information output apparatus;

stores an upper limit value for the cumulative value; and issues a warning indicating how many more times the series of X-ray imaging operations can be performed or how many more the simple X-ray imaging operations can be performed until the upper limit is reached based on the imaging execution conditions of the series of X-ray imaging operations.

11. A non-transitory computer-readable recording medium storing a program causing a computer of an information output apparatus to obtain imaging execution conditions from a radiation generation apparatus regarding a series of X-ray imaging operations;

determine a continuous imaging dose in the series of X-ray imaging operations;

output information based on a number of simple X-ray imaging operations as information pertaining to a continuous imaging dose, the continuous imaging dose being a dose in a series of X-ray imaging operations;

store a cumulative value of the number of simple X-ray imaging operations per a predetermined period for the subject in a storage of the information output apparatus;

store an upper limit value for the cumulative value; and issue a warning indicating how many more times the series of X-ray imaging operations can be performed or how many more the simple X-ray imaging operations can be performed until the upper limit is reached based on the imaging execution conditions of the series of X-ray imaging operations.

12. The recording medium according to claim 11, wherein the program causes the computer of the information output apparatus to calculate the information based on the number of simple X-ray imaging operations according to the following formula:

Information based on number of simple X-ray imaging operations=dose in series of X-ray imaging operations/dose per simple X-ray imaging operation.

13. The recording medium according to claim 12, wherein the dose per simple X-ray imaging operation is a reference entrance surface dose (ESD) in simple X-ray imaging used in a facility where a series of X-ray imaging operations are performed.

14. The medium according to claim 12, wherein the dose per simple X-ray imaging operation is a dose corresponding to a subject.

15. The recording medium according to claim 12, wherein the dose per simple X-ray imaging operation is a diagnostic reference level for general imaging.

16. The recording medium according to claim 12, wherein the continuous imaging dose is a dose based on imaging conditions of a subject.

17. The recording medium according to claim 16, wherein the imaging conditions of a subject include at least one of a body position of the subject, a body thickness of the subject, a state of the subject, and a type of examination.

18. The recording medium according to claim 11, wherein the program outputs the information based on a number of simple X-ray imaging operations and the continuous imaging dose as the information pertaining to the continuous imaging dose.

19. The recording medium according to claim 11, wherein the program causes the computer of the information output apparatus to associate a series of X-ray images acquired by the series of X-ray imaging operations with the information pertaining to the continuous imaging dose.

* * * * *